United States Patent
Gilby et al.

[11] Patent Number: 5,883,721
[45] Date of Patent: Mar. 16, 1999

[54] APPARATUS AND PROCESS FOR MEASURING ABSORBANCE IN FLUID SAMPLES

[75] Inventors: Anthony C. Gilby, Foxborough; Michael J. Leveille, Northbridge; Joseph M. DeLuca, Mendon, all of Mass.

[73] Assignee: Waters Investments Limited, New Castle, Del.

[21] Appl. No.: 893,823

[22] Filed: Jul. 11, 1997

[51] Int. Cl.[6] .................................................... G01N 21/05
[52] U.S. Cl. ............................................. 356/440; 356/246
[58] Field of Search ....................................... 356/246, 440

[56] References Cited

U.S. PATENT DOCUMENTS

| | | | |
|---|---|---|---|
| 4,011,451 | 3/1977 | Nelson | 356/246 |
| 4,276,475 | 6/1981 | Nelson | 356/246 |
| 4,681,443 | 7/1987 | Bach et al. | 356/246 |
| 4,792,233 | 12/1988 | Irvine | 356/440 |
| 5,146,283 | 9/1992 | Parnope et al. | 356/246 |
| 5,153,679 | 10/1992 | Gilby | 356/440 |
| 5,351,120 | 9/1994 | Jurcik et al. | 356/246 |
| 5,453,620 | 9/1995 | Wadsworth et al. | 356/440 |

*Primary Examiner*—Vincent P. McGraw
*Attorney, Agent, or Firm*—Anthony J. Janiuk

[57] ABSTRACT

Embodiments of the present invention feature devices and methods for analyzing the absorbance spectra of a sample, and a method of making such device. The device comprises a housing having an exterior surface and an interior surface. The interior surface defines a chamber having an input opening and an exit opening defined by rims. The input opening has a first geometric shape and the exit opening has a second geometric shape. Any point about the rim at the input end can be connected by a straight line to any point on the rim of the exit end. The interior surface end of the chamber corresponds to the sum of these lines from the rim of the input opening, to the rim of the exit opening.

17 Claims, 3 Drawing Sheets

APPARATUS AND PROCESS FOR MEASURING ABSORBANCE IN FLUID SAMPLES

FIELD OF THE INVENTION

Embodiments of the present invention relate to analytical photometric devices and methods and, more particularly, to apparatus and methods which provide improved optical performance. The apparatus features a housing having one or more walls forming a chamber for receiving a sample and light. The chamber has an entrance end and an exit end. The entrance end has an entrance opening, defined by a rim having a first geometric shape, to receive light. The exit end has a exit opening, defined by a rim having a second geometric shape, to discharge light. One of the openings cooperates with the slit of the spectral analysis means. Any point on the rim of the entrance opening can be connected by a straight line to any point on the rim of the exit opening. The one or more walls defining the chamber correspond to the sum of the straight lines between the rim of the entrance opening and the rim of the exit opening.

BACKGROUND OF THE INVENTION

In optical detector systems, such as those used in liquid chromatography, sample constituents of interest are identified and quantified by characteristic spectral absorbance or fluorescence. A typical detector device will have a flowcell. The flowcell has a housing defining a chamber for receiving sample. The chamber has an entrance end and a exit end. The entrance end has a entrance opening having a rim. Similarly, the exit end has an exit opening having a rim. The rims separate the exterior of the housing from the one or more walls of the interior surface of the chamber. The openings may have optical windows or lenses. The chamber defines a vessel for receiving a sample.

Sample, held in the chamber, is subjected to light entering the chamber about the entrance opening. Light is discharged at the exit end. The spectrum is analyzed to determine absorption indicative of a chemical. To effect this, a monochromator or spectrograph must co-operate with the sample chamber of the flowcell.

The size and shape of an absorption chamber for a high performance liquid chromatography (HPLC) ultraviolet (UV) to visible (Vis) light detector is a compromise. High light flux passing through the cell is important to achieve a high signal-to-noise-ratio measurement. The cell volume must be kept low to prevent peak spreading and loss of chromatographic resolution. For a given cell volume and optical throughput, the cell path length should be as long as possible to maximize sample absorption. The dimensions of a typical chamber of a conventional HPLC-UV-Vis absorption flowcell are 10 mm long, and 1 mm in diameter. The total volume is about 8 micro liters.

The shape of the chamber is dictated by manufacturing limitations. The typical flowcell chamber is cylindrical or somewhat conical, with a circular cross-section. These chambers can be machined with straight or tapered reamers. The best optical throughput is obtained when one end of the chamber or flowcell is conjugate with the light source and the other end is, or is conjugate with, the primary aperture stop of the optical system.

A further consideration is dictated by the optical system in which the flowcell is used. When a flowcell is incorporated into a spectrometer system, the light beam which passes through the flowcell must also pass through a grating monochromator or a spectrograph. Good spectral resolution in a compact format, requires the use of a narrow slit. The best optical throughput through the monochromator or spectrograph is achieved if the two primary stops of the optical system are imaged, or conjugate with, the grating and slit. Thus the slit ends up being conjugate with (or coincident with) one end of the flowcell and the shape of the other end of the cell corresponds to the beam shape at the grating.

This has led to a problem matching the optics of the most efficient and compact spectrometer to the most efficient flowcell. Typically, one end of the flowcell (round) is imaged onto the spectrometer slit (tall and narrow), and light is lost on the sides of the slit. Alternatively, one end of the round flowcell is the slit. The result is either poor spectral resolution, or low light throughput.

It is desirable to avoid complicated arrays of mirrors and fiber optics to address the problems of matching the optics of the flowcell to the monochromator or spectrograph.

SUMMARY OF THE INVENTION

Embodiments of the present invention feature a device and method for analyzing the absorbance spectrum of a sample, and a method of making such device. One embodiment of the present invention features a device for measuring the absorbance spectrum of a sample. The device comprises a housing having an exterior surface and an at least one interior wall. The interior wall defines a chamber. The chamber has a first end and a second end. The chamber has a first opening at the first end defined by a rim between the one or more walls and the exterior surface of the housing. The chamber has a second opening at the second end defined by a second rim. Similarly, the rim at the second end separates the one or more interior walls from the exterior surface. The first opening has a first geometric shape and the second opening has a second geometric shape. Any point about the rim at the first opening can be connected by a straight line to any point on the rim of the second openings. The interior surface of the chamber corresponds to the second sum of straight lines from the rim of the first opening to the rim of the second opening. Light can be transmitted from any point on the first rim to any point on the second rim with minimal interference from interior walls.

As used herein, the term "any point on the first or second rim" refers to a point about the interior surface tangential to the rim.

As used herein the term "geometric shape" refers to the cross-sectional shape of the chamber at a plane perpendicular to the path of light through the chamber. The term geometric shape refers to the form of the shape in terms of sides and angles rather than size.

Preferably, at least one opening cooperates with means for inputting light into the chamber. Means for inputting light into the chamber may comprise, by way of example, without limitation lenses, optical fibers, mirrors, windows, incandescent and fluorescent bulbs, lasers, arc lamps and the like or a monochromator. Preferably, at least one end is generally circular in shape.

Preferably, at least one opening has a geometric shape that corresponds generally to the shape of a spectrometer slit.

Preferably, the rim of at least one opening has at least one straight line component and, preferably, two straight line or linear components. Thus, the straight line components can be aligned with the straight line elements of a spectrometer slit. As used herein with respect to the rim, the straight line component includes sections of the rim which may have a slight curvature due to the manufacturing process. Preferably, such shape is an elongated elliptical shape or rounded rectangle. Preferably, the cross-sectional area of each opening is approximately equal. Preferably, the cross-sectional area of each opening is approximately equal.

A further embodiment of the present invention features a method of measuring absorbance from a sample. The method comprises the steps of providing a housing having an exterior surface and at least one interior wall. The interior wall defines a chamber. The chamber has an first end and an second end. The first end has a first opening defined by a first rim between the interior wall and exterior surfaces of the housing. The second end has a second opening defined by a second rim between the interior wall and exterior surface of the housing. The first opening at the first end has a first geometric shape and the second opening at the second end has a second geometric shape. Any point along the rim of the first opening and any point of the rim of the second opening can be connected by a straight line. The method further comprises the steps of introducing a sample into the chamber and introducing light into the chamber. Light is introduced through one of the first and second openings and light is monitored at opposite opening. Light exiting the chamber is used for the purpose of spectral analysis.

Preferably, one the openings cooperate with the shape of the monochromator or spectrograph slit to allow increased light throughput.

A further embodiment of the present invention features a method of making a housing for receiving a sample, receiving light and discharging light, for analyzing the absorbance spectrum of such sample. The method comprises the steps of preparing a hole through a housing mass and threading a wire through the opening. The method further comprises the step of performing electrical discharge machining to form a passage having a first opening having a first geometrical shape on one end of the housing mass and a second opening having a second geometrical shape at an opposite end of the housing mass. The wire is compelled to the periphery of the geometric shapes on the ends of the housing about the shortest distance between points on the rim. Thus, first opening and second opening are made having a rim about the housing in which any point on the rim of the first opening can be connected by a straight line to any point on the rim of the second opening.

Embodiments of the present invention provide for improved throughput of light by a factor of two to three without any loss of spectral resolution or measure in volume of the cell.

These and other features of the present invention will be apparent to those skilled in the art upon viewing the drawings and reading the detailed description of the invention which follow.

DETAILED DESCRIPTION OF THE DRAWINGS

Figure 1:
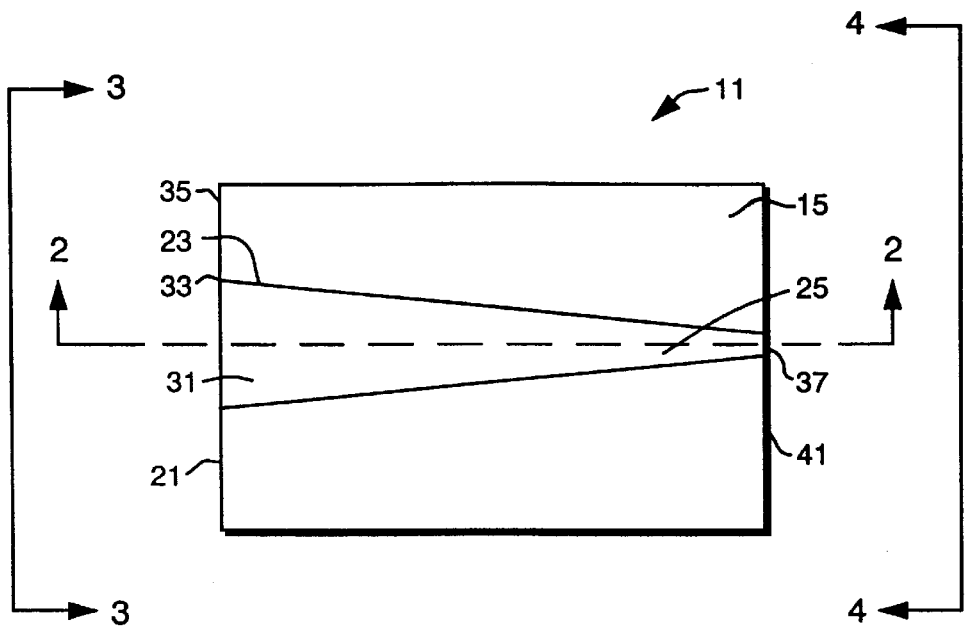
FIG. 1 is a cross-sectional view of a device embodying features of the present invention.

The present invention will be described in detail with respect to analytical photometric devices and methods, and methods of making such devices. Individuals skilled in the art will readily recognize that embodiments of the present invention have broad applicability and the present disclosure is not intended to be limiting. Rather, the present disclosure describes what is now considered the best method of making and using the present invention.

A device embodying features of the present invention, generally designated by the numeral 11, is depicted in FIGS. 1–4. Device 11, is intended to be used in an analytical photometric apparatus having light source means, spectral analysis means and light detection means. Such analytical photometric apparatus, light source means, spectral analysis means and light detection means are known in the art. (See, by way of example, U.S. Pat. No. 5,153,679). A photometric apparatus will be described in greater detail with respect to FIG. 7.

Device 11 has a housing 15 which has an exterior surface 21 and an interior wall 23. Interior wall 23 defines a chamber 25. Chamber 25 has a first opening 31 defined by a rim 33 between the interior wall 23 and exterior surface 21 of housing 15. First opening 31 defines a first end 35 of housing 15.

Figure 3:
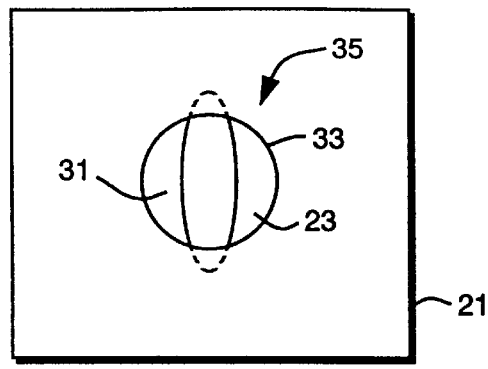
FIG. 3 is a view of a device embodying the features of present invention take along lines 3—3 of FIG. 1.

As best seen in FIG. 3, first opening 31 has a geometric shape in the form of a circle. Other geometric shapes comprising by way of example ovals, squares and rectangles may be used. The geometric shape of first opening 31 is preferably chosen to maximize the throughput of light through the spectrometer system.

Figure 2:
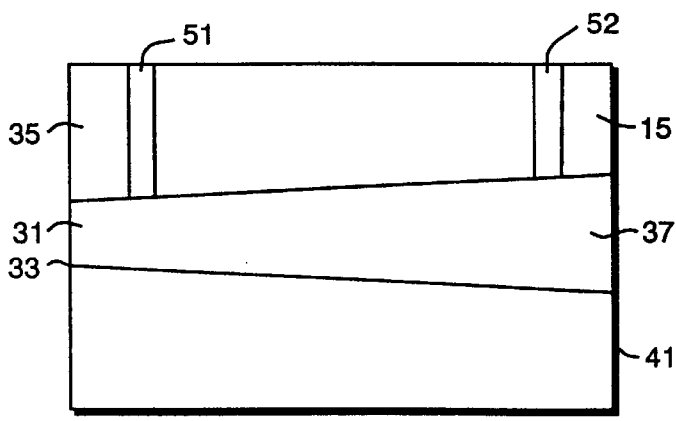
FIG. 2 is a cross-sectional view of a device embodying features of the present invention taken along lines 2—2 of FIG. 1.
Figure 4:
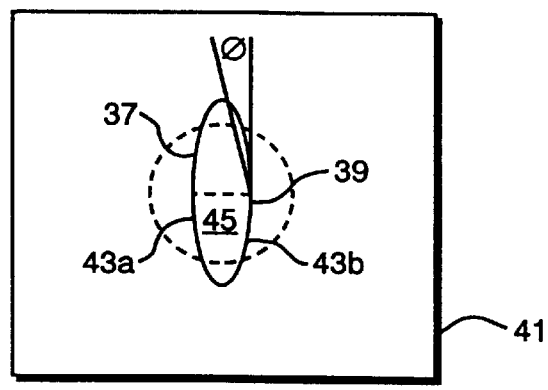
FIG. 4 is a view of a device embodying features of the present invention taken along lines. 4—4 of FIG. 1.

Turning now to FIGS. 1,2 and 4, chamber 25 has a second opening 37 defined by a second rim 39 between the interior wall 23 and exterior surface 21 of housing 15. Second opening 37 defines a second end 41 of housing 15. Second opening 37 has a geometric shape distinct from the geometric shape of first opening 31.

Whereas first opening 31 has a circular geometric shape, second opening 37 has an ovoid, rounded rectangular or almost rectangular geometric shape. The ovoid geometric shape illustrated allows second opening 37 to cooperate with a slit [not shown]. Such slits typically comprise straight or linear components. Second opening 37 has linear or straight sections 43a and 43b to efficiently allow light into or out of such opening in cooperation with a slit. Straight sections 43a and 43b may have a slight curvature due to the manufacturing process. Straight sections 43a and 43b are sections comprising, 50 to 70% of the perimeter of second opening 37. Such sections are defined by a curvature having an angle θ deviating no more than approximately ten degrees from a tangential line at a point across the narrowest radius, designated by line 45. Preferably, second opening 37 has a shape with a length dimension greater than the diameter of first opening 31.

First opening 31 and second opening 37 may have any geometric shape. Preferably, the geometric shape of the first opening 31 and the geometric shape of the second opening 37 are chosen to maximize the throughput through the spectrometer system. Preferably, the cross-sectional shapes of first opening 31 and second opening 37 are approximately equal. Preferably, the geometric shape of the second opening 37 is chosen to cooperate with slit means [not shown]. Housing 15 may also comprise fittings [not shown] to secure light input means and output means [not shown] to the device 11 or to form a contained vessel in chamber 25. Such light input and output means comprise windows, lenses, fiber optics, and the like. Such fittings are known in the art and are omitted from this discussion for purposes of clarity.

Preferably, the interior wall 23 of chamber 25 is polished to provide a highly reflective surface. The interior wall 23 comprises a complex shape defined by the envelope of straight lines extending from every point on rim 33 to each point on rim 39. Light traverses the chamber 25 between rim 33 to rim 39, without interference with interior wall 23 or excess volume.

Preferably, as best seen in FIG. 2, housing 15 has a sample entrance opening 51 and a sample exit opening 53. Sample entrance opening 51 allows samples to be introduced into chamber 25 for absorbance analysis. Sample exit opening 53 allows removal of sample upon the completion of the analysis. Sample entrance opening 51 is placed in communication with a source of sample [not shown]. Sample exit opening 53 is placed in communication with a collection vessel [not shown] for recovering waste samples. Entrance opening 51 and sample exit opening 53 are preferably equipped with fittings [not shown], known in the art, to cooperate with a source of sample and waste receptacles. Sample entrance opening 51 and sample exit opening 53 may also be machined into the first end 35 and second end 41.

Figure 5:
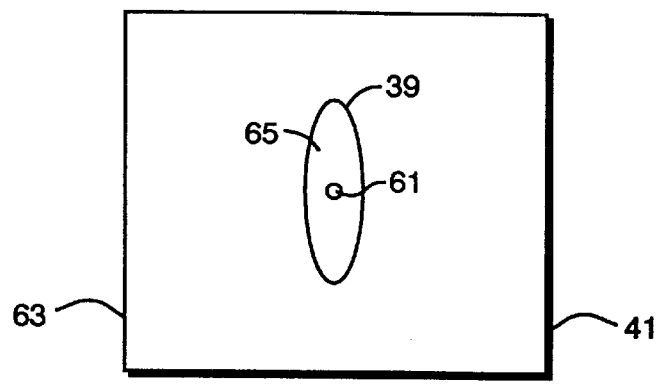
FIGS. 5 and 6 is a view of a housing mass illustrating a method of manufacture embodying features of the present invention.
Figure 6:
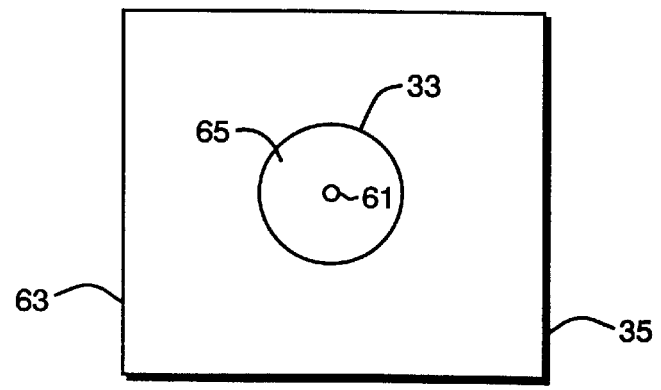

Embodiments of the present device 11 are preferably made by electrical discharge machining. An embodiment of the present invention is directed to a method of making the device 11. This method is described now with respect to FIG. 5 and 6. A pilot hole 61 is made in a housing mass 63. Preferably, pilot hole 61 would be through the center of the block and, is a stepped hole. Housing mass 63 will become housing 15 of FIGS. 1–4.

Hole 61 receives a wire [not shown] for performing electrical discharge machining. The wire, under electrical discharge enlarges the pilot hole until it is finally, compelled along the intended rims 39 and 33. Preferably, during cutting, the wire visits all points around rim 39 from each point on rim 33.

The interior surface 23 can be polished by forcing an abrasive paste through the chamber 25 under high pressure. Sample entrance opening 51 and sample exit opening 53 are drilled into housing mass 61 by conventional means or machined into the end faces of the housing mass 63. Sample entrance openings 51 and sample exit opening 53 may also be equipped with fittings.

Figure 7:
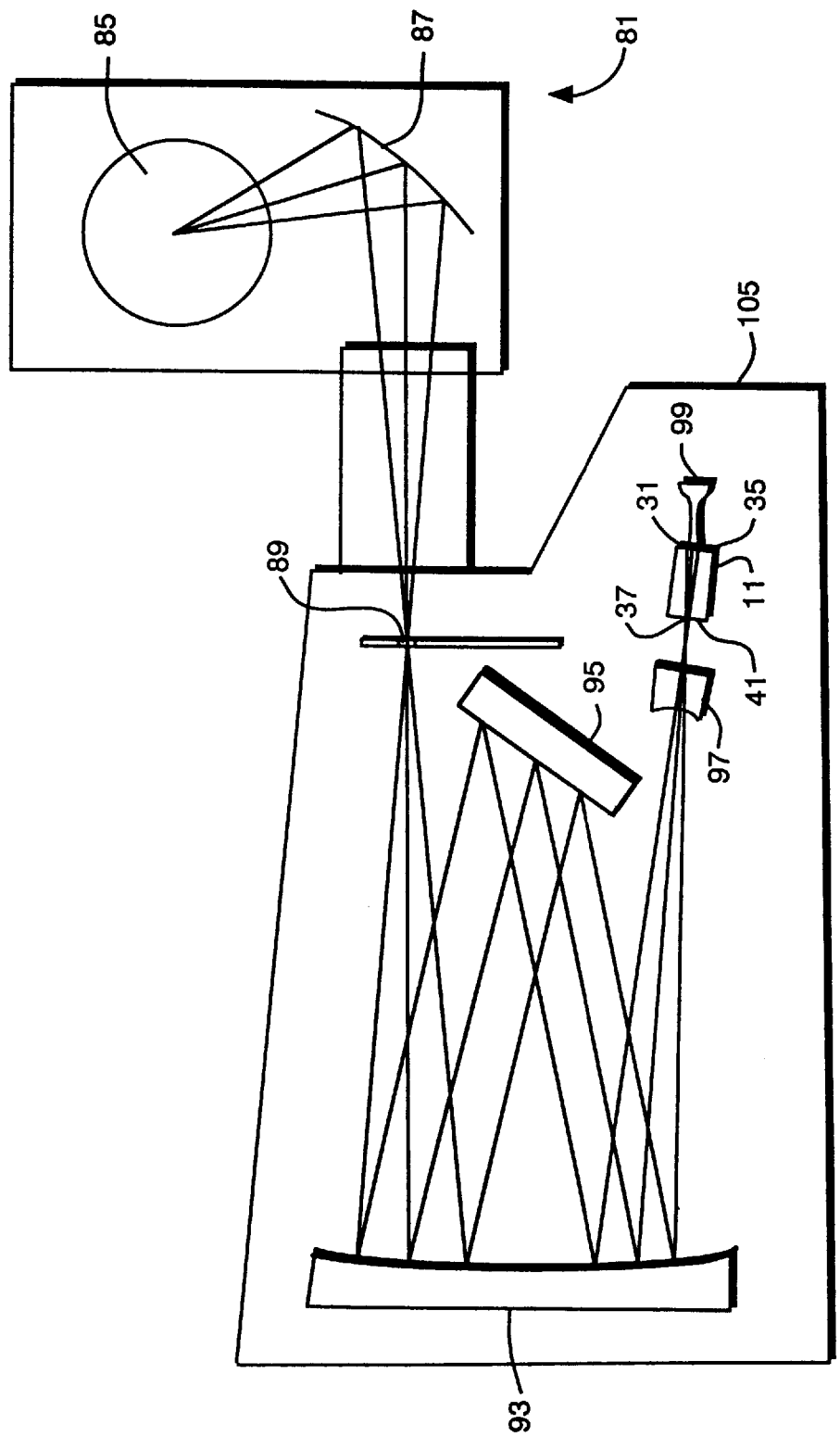
FIG. 7 is a schematic of an absorbance detector embodying features of the present invention.

The operation of the device will be described with respect to a monochrometer apparatus depicted in schematic form in FIG. 7. A monochromator apparatus, generally designated by the numeral 81, is comprised of the following major components: light source 85, first mirror 87, slit 89, second mirror 93, grating 95, beam splitter 97, flowcell 11, and detector 99. An instrument housing, generally designated by the numeral 105, is illustrated, without detail, to simplify this discussion.

Light produced by light source 85 is focused by the first mirror 87 on slit 89. Light emerging from the slit is collimated by mirror 93 and directed to grating 95. Diffracted light of a particular wavelength is focused by 93 on the entrance to the flowcell. Opening 31 and 37 as preferably equipped with lenses or optical windows (not shown). The chosen wavelength depends on the angle of the grating. A portion of the beam is diverted by beam splitter 97 to a reference detector (not shown). Housing 15 of flow cell 11 is held within a monochromator apparatus 85 by securing means well known in the art.

Now turning to FIG. 2, sample is placed in chamber 25 through sample opening 51. Light of substantially a single wavelength is directed into chamber 25 via second opening 37. Light entering about rim 39 may traverse through chamber 25 along a straight line to any point on first opening 31 about first rim 33 without interference from the interior surface 23. Consequently, light enters the slit-shaped end of the cell, which co-operates with the grating monochrometer to preserve spectral resolution. The elongated opening of the flow cell 11 has increased area for high light throughput.

The beam of light exiting flow cell 11, has a cross-sectional shape which cooperates with first opening 31 of first end 35. Light exits the flow cell 11 from first opening 31. The beam cross-sectional shape at first opening 31 is established by a mask on mirror 93 and a lens which is the cell window at second opening 37.

In spectrographic apparatus, where the flowcell is placed before the spectrograph entrance slit, the flow cell 11 may receive light at first opening 31 and allow light to exit at second opening 37. The cross-sectional shape of the mask on mirror 93 determines the area used of the differential grating. In this way, the optical through put of the flow cell is matched to the optical through put of the monochromator.

In spectrographic apparatus, for example when a diode array detector is used, the flowcell is placed before the spectrograph entrance slit. In this case the light may enter first opening 31 which shape cooperates with that of this spectrograph grating, and second opening 37 which shape cooperates with that of the spectrograph entrance slit.

Light entering chamber 25 interacts with sample which imparts a characteristic or absorbance spectrum to the light. Light traverses the chamber 25 to create a absorbance pattern which is characteristic or unique to one or more components of the sample. This absorbance is measured by detector 99, best seen in FIG. 7. Sample is removed from chamber 25 through sample exit opening 53.

Embodiments of the present invention features a photometric analytical device which can be readily machined. The device features improved light throughput without a complicated array of mirrors or fiber optic image transference. The present device and method prevents the loss of light which normally occurs on the sides of the slit. Embodiments of the present invention avoid an anamorphic changes of a circular image to a substantially rectangular image. Indeed, embodiments of the present invention provide for an increase of optical throughput by a factor of two to three without loss of spectral resolution.

The device of the present invention can readily be incorporated in apparatus and processes for measuring light absorbance or fluorescence in liquid of the type described in U.S. Pat. No 5,153,679.

Thus, preferred embodiments of the invention have been described. However, the present invention is capable of variation and modification and, should not be limited to the precise details set forth herein but should include such changes and alterations as fall within the purview of the following claims.

We claim:

1. An apparatus for determining the absorbance spectrum of a sample, comprising: a housing having an exterior surface and at least one interior wall, said interior wall defining a chamber, said chamber having a first opening defined by a first rim between the interior wall and exterior surface, said first opening having a first geometric shape, said chamber having a second opening defined by a second rim between the interior wall and the exterior surface, said second opening having a second geometric shape which geometric shape is different from said first geometric shape, at least one of said openings comprising an inlet opening for receiving light and at least one of said opening comprising an exit opening for discharging light, said interior wall comprising the sum of lines between said first and second rims to allow light transmission from any point about the rim of one of said openings to a point about the rim of said opposite opening.

2. The apparatus of claim 1 wherein at least one of said openings corresponds to the shape of a spectrometer slit.

3. The apparatus of claim 1 wherein at least one of said openings has a linear component.

4. The apparatus of claim 1 wherein at least one of said openings is in communication with light inputting means.

5. The apparatus of claim 1 where is at least one opening has a circular shape and at least one opening has an ovoid shape.

6. A method of determining the absorbance spectrum of a sample comprising the steps of:
   a. providing a housing having an exterior surface and at least one interior wall, said interior wall defining a chamber, said chamber having a first opening defined by a first rim between the interior wall and said exterior surface, said first opening having a first geometric shape, said chamber having a second opening defined by a second rim between the interior wall and the exterior surface, said second opening having a second geometric shape which geometric shape is different from said first geometric shape, at least one of said openings comprising an inlet opening for receiving light and at least one of said opening comprising an exit opening for discharging light, said interior wall comprising the sum of lines between said first and second rims to allow light transmission from any point about the rim of one of said openings to a point about the rim of said opposing opening;
   b. placing a sample in said chamber;
   c. directing light into said chamber through one of said openings; and
   d. receiving light from said chamber through one of said openings to create a spectrum of light absorbance.

7. The apparatus of claim 6 wherein at least one of said openings corresponds to the shape of a spectrometer slit.

8. The apparatus of claim 6 wherein at least one of said openings has a linear component.

9. The apparatus of claim 6 wherein at least one of said openings is in communication with light inputting means.

10. The apparatus of claim 6 wherein at least one opening has a circular shape and at least one opening has an ovoid shape.

11. A method of making a device for determining the absorbance spectrum of a sample comprising the step of creating a hole in a housing mass and threading a wire through said hole, performing electrical discharge machining by directing a current through said wire and compelling said wire through said housing mass, to form a housing having an exterior surface and at least one interior wall, said interior wall defining a chamber, said chamber having a first opening defined by a first rim between the interior wall and exterior surface, said first opening having a first geometric shape, said chamber having a second opening defined by a second rim between the interior wall and the exterior wall surface, said second opening having a second geometric shape which geometric shape is different from said first geometric shape, at least one of said openings comprising an inlet opening for receiving light and at least one of said opening comprising an exit opening for discharging light, and said interior wall comprising the sum of lines between said first and second rims to allow light transmission from any point about the rim of one of said openings to any point about the rim of said second opening.

12. The method of claim 11 wherein said wire is compelled allowing the periphery of the first rim and second rim.

13. The method of claim 11 wherein at least one of said openings corresponds to the shape of a spectrometer slit.

14. The method of claim 11 wherein at least one of said openings has a linear component.

15. The method of claim 11 wherein at least one of said openings corresponds in shape to light inputting means.

16. The method of claim 11 wherein the shape of the non-slit end corresponds with the beam shape at the wavelength-selecting grating.

17. The method of claim 11 wherein at least one opening has a circular shape and
   at least one opening has an ovoid shape.

* * * * *